(12) United States Patent
Benisty et al.

(10) Patent No.: US 10,955,619 B2
(45) Date of Patent: *Mar. 23, 2021

(54) ADAPTOR FOR CONNECTING A MEDICAL LASER TO A FLEXIBLE WAVEGUIDE OR AN ARTICULATED ARM

(71) Applicant: LUMENIS LTD., Yokneam Ilit (IL)

(72) Inventors: Eyal Benisty, Kfar Hachoresh (IL); Stanislav Kramer, Haifa (IL); Assaf Gelstein, Haifa (IL)

(73) Assignee: LUMENIS LTD., Yokneam (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/862,280

(22) Filed: Apr. 29, 2020

(65) Prior Publication Data

US 2020/0348470 A1 Nov. 5, 2020

Related U.S. Application Data

(63) Continuation of application No. 14/874,491, filed on Oct. 5, 2015, now Pat. No. 10,746,936, which is a (Continued)

(30) Foreign Application Priority Data

Apr. 15, 2013 (GB) ..................................... 1306832

(51) Int. Cl.
*A61B 6/00* (2006.01)
*G02B 6/35* (2006.01)
(Continued)

(52) U.S. Cl.
CPC .......... *G02B 6/3514* (2013.01); *A61B 18/201* (2013.01); *G02B 6/4296* (2013.01);
(Continued)

(58) Field of Classification Search
CPC ........ B25J 9/0084; A61B 90/50; A61B 17/29; A61B 2017/00991; A61B 18/201;
(Continued)

(56) References Cited

U.S. PATENT DOCUMENTS 4,532,400 A   7/1985  Masahiro
4,550,240 A   10/1985 Masahiro et al.
(Continued)

FOREIGN PATENT DOCUMENTS

EP   0093005   11/1983
EP   2169435   3/2010
(Continued)

*Primary Examiner* — Rex R Holmes
*Assistant Examiner* — Sana Sahand
(74) *Attorney, Agent, or Firm* — Isus Intellectual Property PLL; Anthony Jason Mirabito

(57) ABSTRACT

A dual port switching apparatus (12) comprising a connection part for mounting to a base unit (11), an input beam port to receive a main laser beam from a base unit (11) in an input optical path (22), a first output port (14) for connection to a flexible wave guide, a second output port (15) for connection to an articulated arm (16), and a switching element (56) moveable between a first position and a second position to direct an input beam to one of the first output port (14) and the second output port (15).

7 Claims, 12 Drawing Sheets

Related U.S. Application Data continuation of application No. PCT/IB2014/060704, filed on Apr. 14, 2014.

(51) Int. Cl.
*A61B 18/20* (2006.01)
*G02B 6/42* (2006.01)
*A61B 18/00* (2006.01)

(52) U.S. Cl.
CPC ............ *A61B 2018/00017* (2013.01); *A61B 2018/00172* (2013.01); *A61B 2018/00696* (2013.01); *A61B 2018/00744* (2013.01); *A61B 2018/2025* (2013.01); *G02B 6/4292* (2013.01)

(58) Field of Classification Search
CPC .. A61B 2018/00172; A61B 2018/2025; A61B 2018/203
USPC .......................................................... 606/10
See application file for complete search history.

(56) References Cited

U.S. PATENT DOCUMENTS

| | | |
|---|---|---|
| 5,729,643 A | 3/1998 | Hmelar |
| 2002/0072736 A1 | 6/2002 | Tierney |
| 2007/0147752 A1 | 6/2007 | Weisberg |
| 2012/0321259 A1 | 12/2012 | Lu et al. |
| 2013/0110093 A1 | 5/2013 | Yee |
| 2014/0121653 A1 | 5/2014 | Abe |
| 2015/0148786 A1 | 5/2015 | Plunkett |

FOREIGN PATENT DOCUMENTS

| | | |
|---|---|---|
| FR | 2570509 | 3/1986 |
| JP | 2012239698 | 10/2012 |

ADAPTOR FOR CONNECTING A MEDICAL LASER TO A FLEXIBLE WAVEGUIDE OR AN ARTICULATED ARM

RELATED APPLICATIONS

This application is a continuation application of U.S. application Ser. No. 14/874,491, filed Oct. 5, 2015, which is a continuation of PCT/IB2014/060704, filed Apr. 14, 2014, which claims priority to Great Britain Application No. 1306832.5, filed Apr. 15, 2013.

FIELD OF THE INVENTION

This invention relates to an adaptor for a medical laser unit, a medical laser unit, a method of adapting a base unit for a medical laser unit, a control unit for a medical laser unit and a method of operating a medical laser unit.

BACKGROUND OF THE INVENTION

Lasers have found a number of applications in medical procedures. Using suitably focussed and powerful laser beams, tissues can be excised, ablated or cut with fine control and with reduced bleeding. Example treatments are excision and vaporization of benign and cancerous growths and fibromas, and aesthetic treatments. Conventionally, a $CO_2$ laser is used as the source of the beam producing light at a wavelength of 10.6 Because this wavelength is not suitable for transmission through conventional optical fibres, where it would be absorbed by the silica, it is known to use either hollow flexible waveguides, or internally reflective articulated arms, to direct the beam to the site of operation.

SUMMARY OF THE INVENTION

According to a first aspect of the invention there is provided a dual port switching apparatus comprising a connection part for mounting to a base unit, an input beam port to receive a main laser beam from a base unit, a first output port for connection to a flexible wave guide, a second output port for connection to an articulated arm, and a switching element moveable between a first position and a second position to direct an input beam to one of the first output port and the second output port.

The switching element may comprise a mirror.

The mirror may be moveable in a linear direction between the first position and the second position.

The adaptor may comprise a linear actuator operable to move the switching element between the first position and the second position.

The adaptor may comprise an auxiliary guide beam source, and a beam combiner to direct an auxiliary guide beam to the first output port.

The first output port may be for connection to a hollow wave guide.

The auxiliary guide beam may be controllable to direct the auxiliary guide beam into a cladding layer of the hollow wave guide.

The input beam port may define an input beam path extending generally vertically, one of the first and second output ports may extend substantially vertically in line with the input beam path, and the other of the first output port and second output port may extend at an angle relative to the input beam path.

In one of the first position and of the second position the switching element may extends into the input beam path, and in the other of the first position and second position, may be spaced from the input beam path.

The adaptor may comprise a pressurized gas connection to allow supply of pressurized gas to the first output port.

According to a second aspect of the invention there is provided a medical laser unit comprising a base unit, the base unit comprising a main laser source and a base unit output port, and an adaptor according to the first aspect of the invention, the adaptor being mounted on the base unit such that the input beam port is connected to the base output beam port to receive the main beam from the main laser source.

The main laser source may comprise a $CO_2$ laser to provide the main beam.

The base unit may comprise a main guide beam source and alignment optics wherein the main laser guide beam may be aligned with the CO2 laser beam.

The apparatus may comprise a control unit operable to control the main laser source.

The medical laser unit may have a user input device to receive user instructions and transmit instructions to the control unit.

The control unit is may be operable to control the switching element.

The medical laser unit may be operable to detect if a flexible wave guide is connected to the first output port.

If a flexible wave guide is detected, the control unit may be operable to control the switching element to direct the $CO_s$ laser beam to the first output port, and control the auxiliary guide beam source.

The medical laser unit may comprised a pressurised gas source and a pressurised gas controller, the control unit being operable to control the pressurised gas controller to direct cooling fluid to one of the first output port and an articulated arm.

According to a third aspect of the invention, there is provided a method of adapting a medical laser apparatus, the medical laser apparatus being a base unit comprising a main laser source and a laser output port, the method comprising the step of providing an adaptor according to the first aspect of the invention, and mounting the adaptor on the base unit such that the input beam port is aligned with the laser beam port.

Where the base unit comprises a control unit, the method may comprise the step of connecting the control unit to the switching element such that the control unit is operable to move the switching element between the first position and the second position.

The method may comprise the step of connecting the control unit to the auxiliary guide beam source such that the control unit is operable to control the auxiliary guide beam.

According to a fourth aspect of the invention there is provided a control unit for a medical laser unit comprising a main laser to generate a main beam, the medical laser unit having an adaptor comprising a first output port, a second output port and a switching element, the control unit being operable to receive an operator input and move the switching element between a first position in which the main beam is directed to the first output port and a second position in which the main beam is directed to the second output port.

According to a fifth aspect of the invention there is provided a method of operating a medical laser unit comprising operating a main laser to generate a main beam, and operating a switching element to move the switching element between a first position in which the main beam is directed to a first output port and a second position in which the main beam is directed to a second output port.

BRIEF DESCRIPTION OF THE DRAWINGS

An embodiment of the invention is described by way of example only with reference to the accompanying drawings wherein.

DETAILED DESCRIPTION OF THE PREFERRED EMBODIMENTS

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before explaining at least one embodiment of the invention in detail, it is to be understood that the invention is not limited in its application to the details of construction and the arrangement of the components set forth in the following description or illustrated n the drawings. The invention is applicable to other embodiments or of being practiced or carried out in various ways. Also, it is to be understood that the phraseology and terminology employed herein is for the purpose of description and should not be regarded as limiting.

Figure 1:
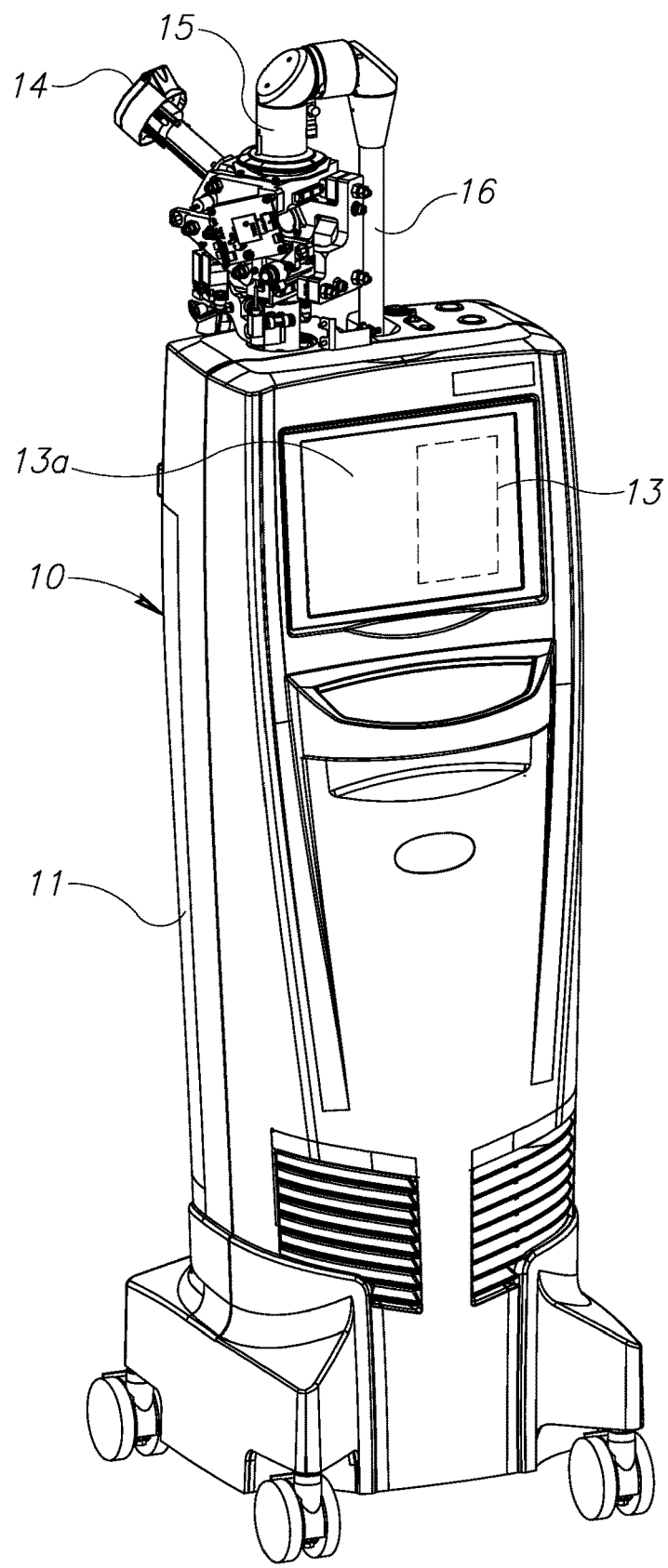
FIG. 1 is a perspective view of a medical laser unit.
Figure 2:
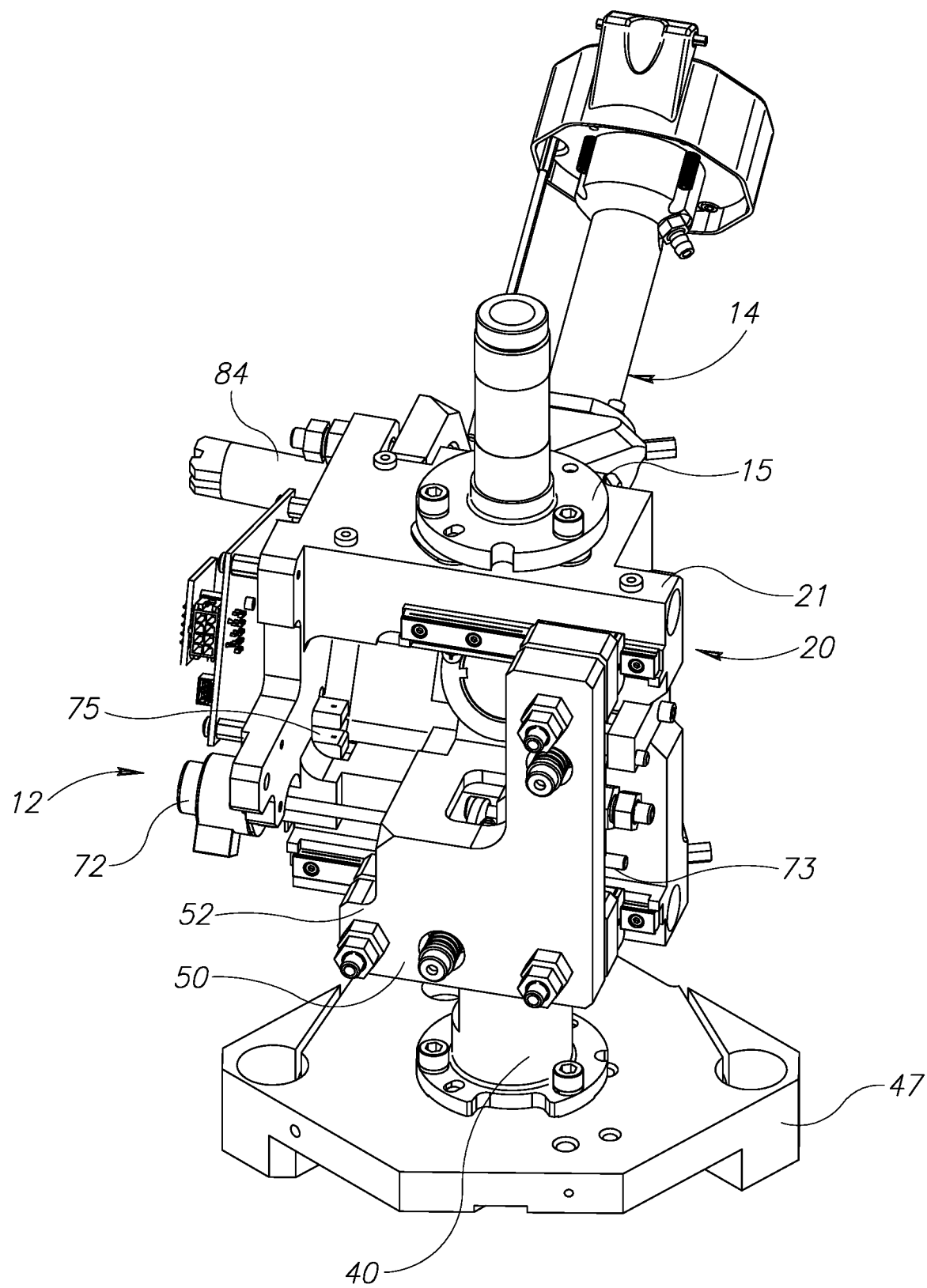
FIG. 2 is a perspective view of an adaptor unit for the apparatus of FIG. 1.
Figure 3:
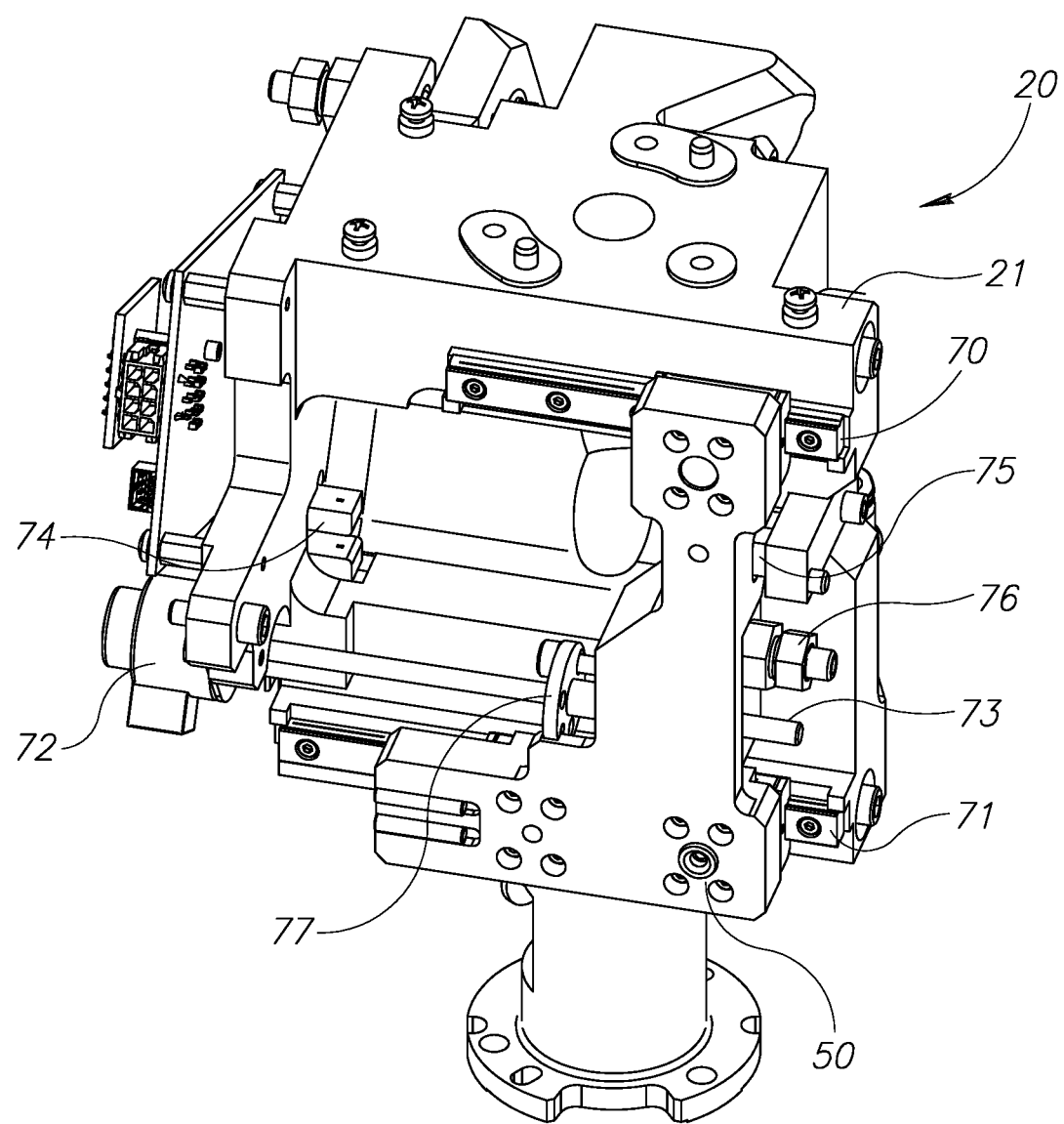
FIG. 3 is a perspective view of the adaptor of FIG. 2 with some elements removed.

Referring now to FIG. 1, a medical laser unit generally embodying the invention is shown at 10. The medical laser unit comprises a base unit 11 and an adaptor 12, which will be described hereafter in more detail. The base unit 11 comprises a main laser source (not shown), in the present example comprising a $CO_2$ laser, to generate a main laser beam with an output wavelength of 10.6 As the main laser beam is in the infrared and so is not visible, a main guide laser (not shown) is also mounted in the base unit 11 to produce a visual main guide beam. Suitable beam combination and collimation optics are provided such that the base unit 11 outputs a main beam comprising the 10.6 µm beam and the main guide beam such that both beams are collimated and co-propagating. The base unit 11 further comprises a control unit shown in dashed outline at 13 and a control screen 13a which is operable to display operating information received from a control unit and to receive operator input to the control unit to control the laser output of the medical laser unit 10. The main beam and main guide beam are transmitted to the adaptor 12. The adaptor 12 has a first output port 14, for connection to a hollow waveguide, and a second output port 15 for connection to an internally reflective articulated arm 16. The adaptor 12 has a switching element, described below, which is controllable by the control unit 13 to direct the received main beam to one of the first output port 14 and second output port 15 as directed by an operator. Although not shown, it will be apparent that electrical connections are provided between the control unit 13 and the functional elements of the adaptor 12 so that the operation of the adaptor 12 can be monitored and controlled as appropriate. Where the adaptor 12 has a separate auxiliary control unit, this may be connected to the control unit 13 such that they operate as a single controller, preferably in a manner transparent to the operator.

The adaptor 12 will now be described in more detail with reference to FIGS. 2 to 8. The adaptor 12 comprises an opto-mechanical chassis generally shown at 20. This is a solid, rigid body which serves as a reference surface with fixed location stops onto which other components can be mounted.

Figure 5:
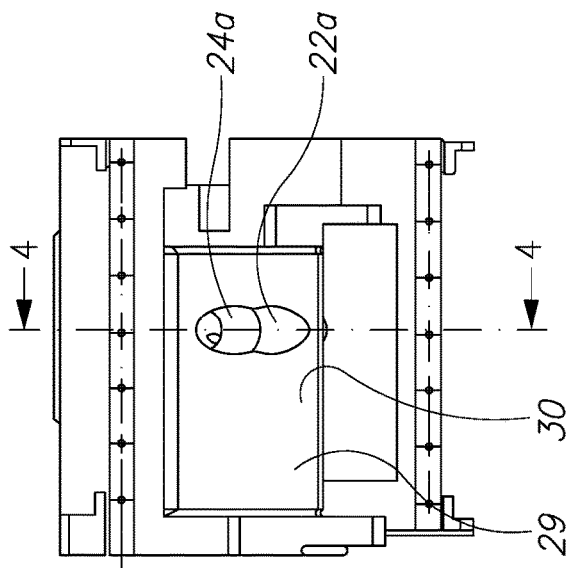
FIG. 5 is a view in direction 5 of part of the adaptor of FIG. 3.
Figure 6:
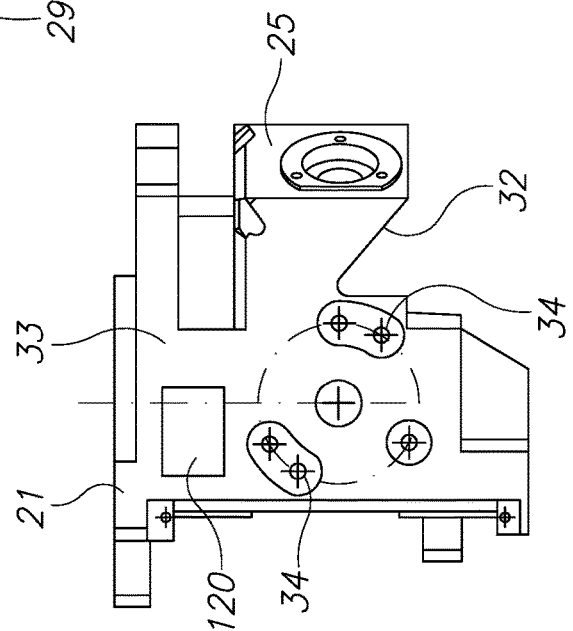
FIG. 6 is a plan view of the adaptor of FIG. 3.
Figure 4:
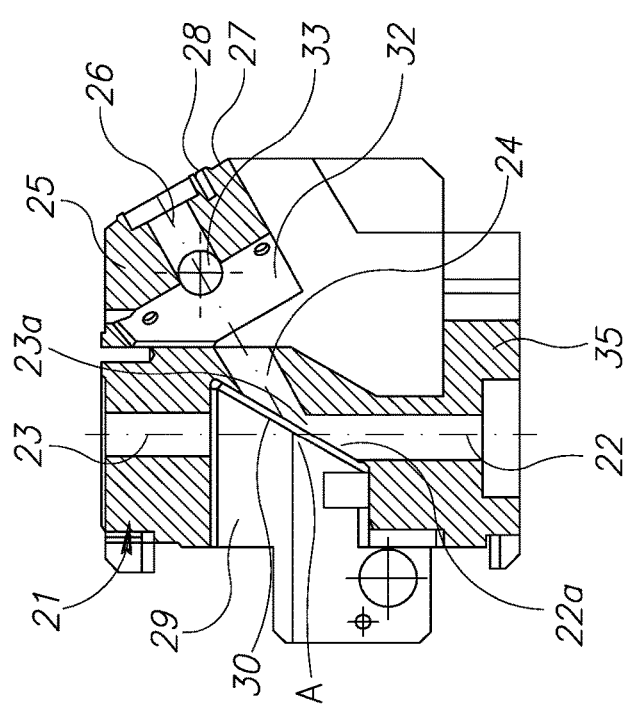
FIG. 4 is a section on line 4-4 of FIG. 3.
Figure 7:
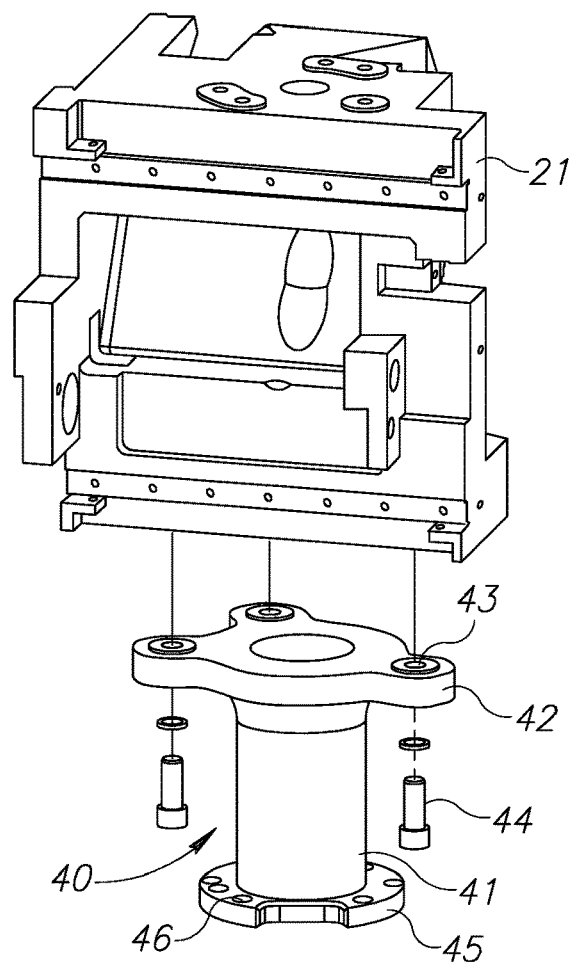
FIG. 7 is a exploded perspective of a support part of the adaptor of FIG. 3.
Figure 8:
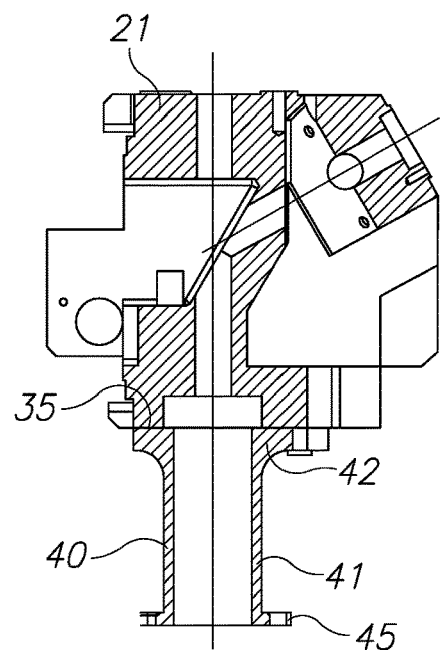
FIG. 8 is a cross-sectional view of the adaptor of FIG. 7.

As seen in FIG. 4 to FIG. 6, the opto-mechanical chassis comprises a main body 21 with a number of ports and recesses defined therein. The main body 21 is milled from aluminium to provide suitable rigidity, coefficient of thermal expansion and robustness. Preferably, the surfaces are also finished, for example by anodising, to produce a protective surface which has a matt texture to diffuse potentially hazardous laser reflections.

Within the main body 21, input beam path 22 extends vertically from a lower part of the body 21. First output beam path 23 and second output beam path 24 lead to the first output port 14 and second output port 15 respectively. First output beam path 23 is co-planar with the input beam path 22 and second output beam path 24, and is inclined at an oblique angle relative to the input beam path 22. The second output beam path 24 is co-linear with input beam path 22. The rigid body 21 has an output support part best shown at 25, which has a third output beam path 26 extending therethrough which is co-linear with the first output beam path 24. The support part 25 has an inclined connection face 27 which is perpendicular to the third output beam path 26 and provided with mounting points 28.

Channel 29 extends in a linear manner into the main body 21 and has an angled inner face 30. Input beam path 22 and first beam path 23 have respective openings 22a, 23a in the angled surface 30, and the input, first and second beam paths 22, 23, 24 converge at point A within channel 29.

To provide for an auxiliary guide beam as discussed in more detail below, the opto-mechanical chassis 21 comprises an auxiliary guide laser support 31 extending alongside the support part 25. The support part 25 has an inclined rear surface 32 to support an auxiliary guide beam combiner as discussed in more detail below and a transversely extending auxiliary guide beam path 32a extending towards a corresponding board in the auxiliary guide beam support arm 31.

At an upper surface 33 thereof, the main body 21 is provided with connection points 34 for connection to a beam combiner comprising the second output port 15 to direct the beam to an articulated arm 16.

The opto-mechanical chassis 20 further comprises a vertical support 40, on which the main body 21 is supported. In this example the vertical support 40 comprises a generally cylindrical body 41 defining an input beam port. An upper flange 42 engages a lower surface 35 of the body 21 and comprises a plurality of apertures 43 through which bolts 44 may pass to be received in threaded apertures (not shown) in the body 21. At the lower end the vertical support 40 comprises an outwardly extending flange 45 with apertures 46 therein to enable the vertical support 40 to be connected to an optical bench surface 47 provided at the upper surface of the base unit 11.

Figure 9:
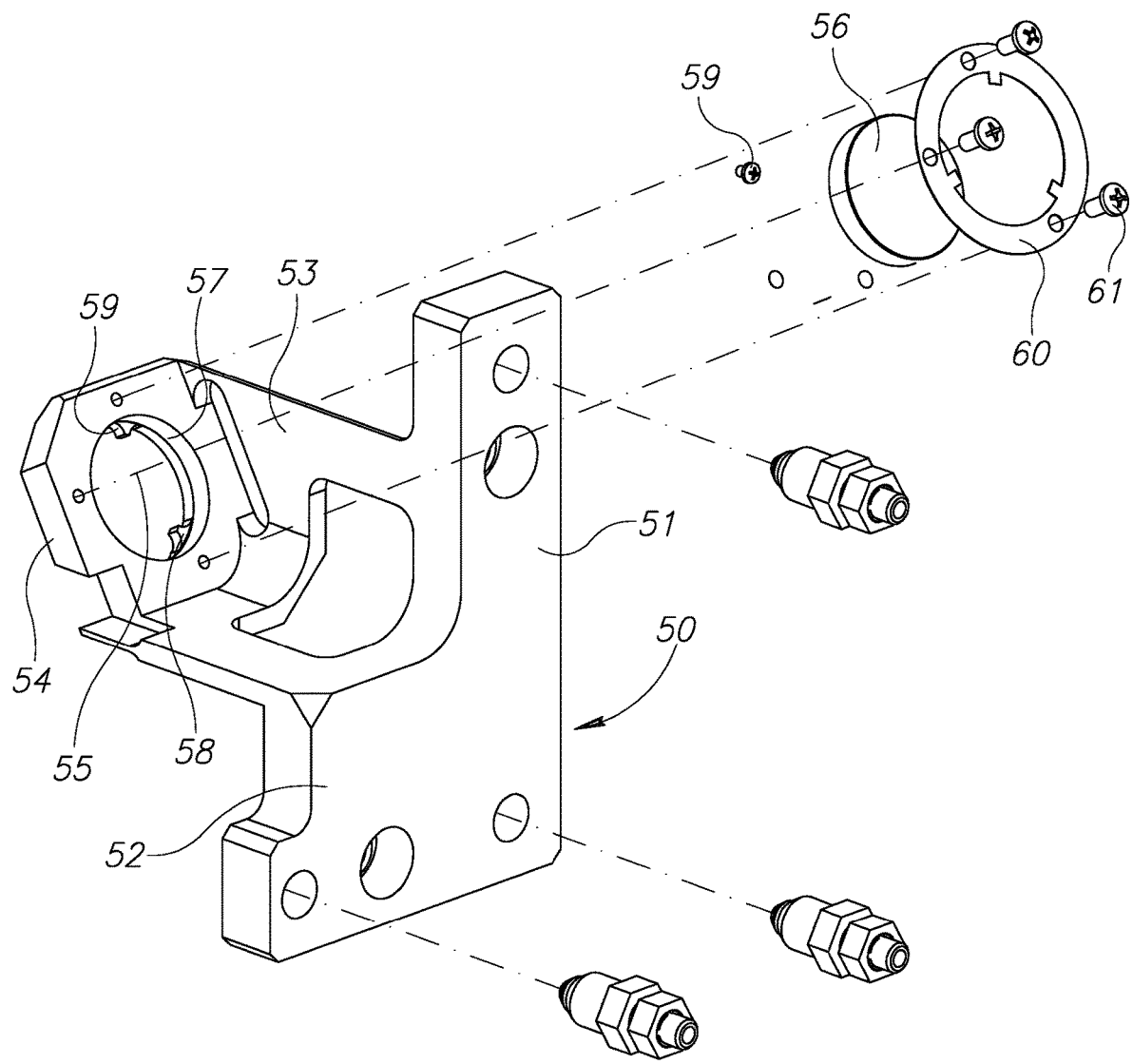
FIG. 9 is a perspective view on a larger scale of part of a switching apparatus for use in the adaptor of FIG. 3.

To switch the main beam, a switching apparatus or mirror assembly is shown generally indicated at 50. The control switch comprises a mirror mount 51 best shown in FIG. 9 which has a vertical support plate 52. The vertical support plate 52 comprises a mirror support arm 53 which is dimensioned to be received in channel 29. At the end of support arm 53 there is provided a mirror support plate 54 which is inclined relative to the vertical support plate 52. The mirror support plate 54 has a circular aperture 55 in which is received a plane mirror 56, the reflective surface of the mirror being directed downwardly and to the left as shown in FIG. 9. Although the present embodiment uses a plane mirror, it will be apparent that a curved mirror may be used if desirable, for example for focussing or beam conditioning purposes.

To support the mirror 56, aperture 55 has an inwardly directed lip 57. Three recesses 58 are located within the lip 57 which receive bearing balls 59, the bearing balls 59 defining a correctly aligned surface. The mirror 56 when in position is supported by these bearing balls 59. A retaining ring 60 is held in place by screws 61 against the back of the mirror 56.

Figure 10:
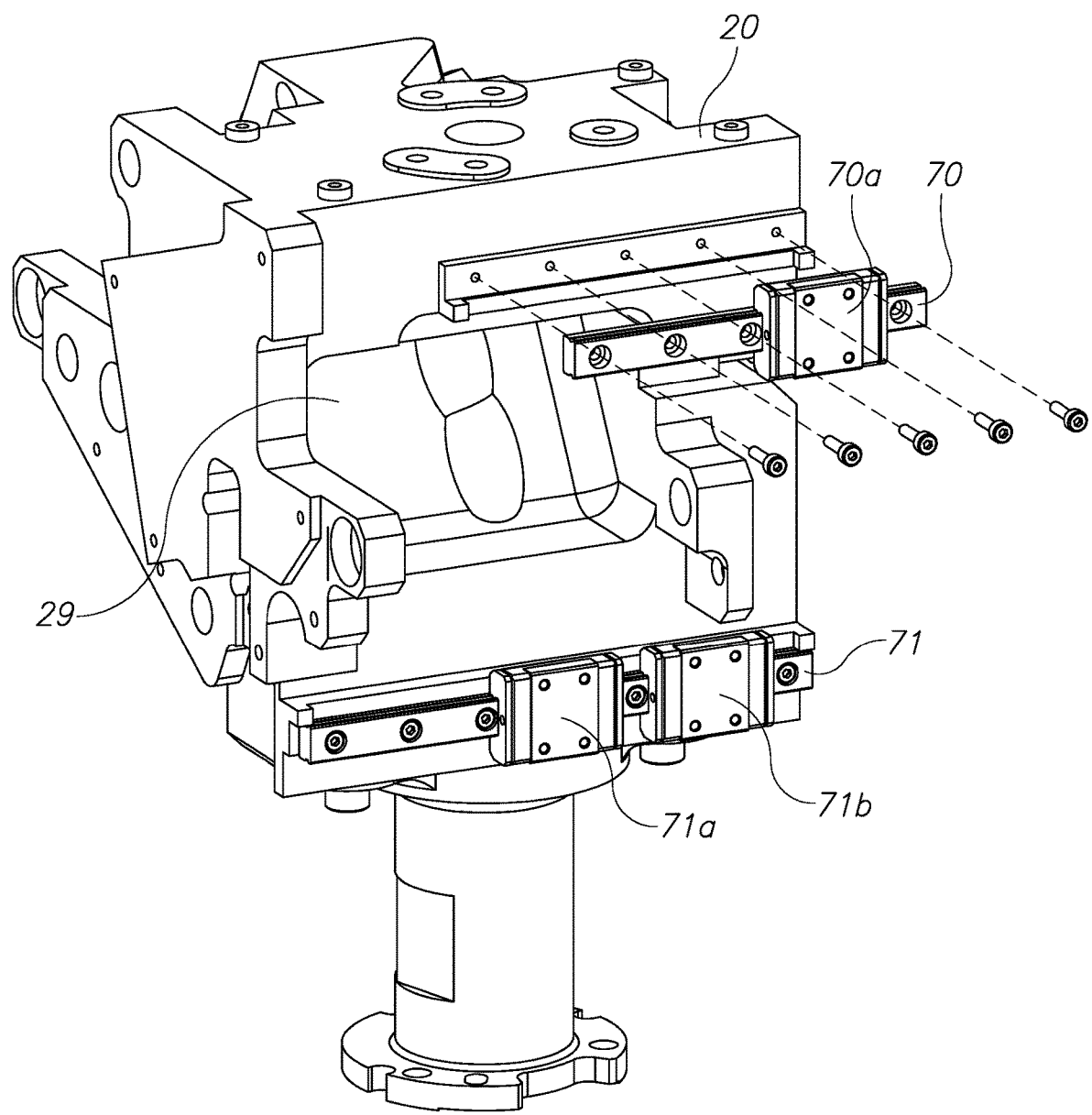
FIG. 10 is a partly exploded perspective view from above of the adaptor of FIG. 3 showing guide rails for the switching apparatus of FIG. 9.

To provide for sliding movement of the mirror assembly 50, the opto-mechanical chassis 20 is provided with horizontally extending guide rails 70, 71 disposed above and below the channel 29. FIG. 10 shows lower guide rail 71 in position and upper guide rail 70 in the correct orientation for connection to the chassis 20. Upper guide block 70a is slidably mounted on the upper guide rail 70, and lower guide blocks 71a, 71a are slidably mounted on the lower guide rail 71. Vertical support plate 51 is connected to the guide blocks 70a, 71a, 71b such that the mirror assembly 50 is moveable lengthways of the channel 29.

To provide for controlled sliding movement of the mirror assembly 50, in the present example a linear actuator is provided comprising a stepper motor 72 connected to a threaded rod 73 extending through a suitable threaded nut 77. Driving the stepper motor 72 causes the rod 73 to rotate and hence causes linear movement of the nut 77 and mirror assembly 50. To avoid motor cleaving or motor sticking, the connection between the mirror assembly 50 and nut 77 preferably comprises a spring or flexible element to provide a degree of freedom between the mount and actuator. In the present example, each step of the stepper motor moves the mirror assembly by 13 μm. Screw 76 has a distal ball end located to provide an end stop for the mirror assembly 50.

The mirror assembly 50 is thus movable by the linear actuator between first and second positions. In the first position, the mirror 56 extends between the input beam path 22 and second input beam path 24, such that the main beam is reflected into first beam path 23. Ideally, the mirror surface passes through point A in FIG. 4. In the second position, the mirror assembly is offset from the beam paths 22, 23, 24 such that the main passes from the input beam path 22 to the second output beam path 24.

To provide for detection of the position of the mirror assembly 50, optical sensors 74, 75 are provided to confirm when the mirror assembly 50 is in the first position or second position.

Figure 11:
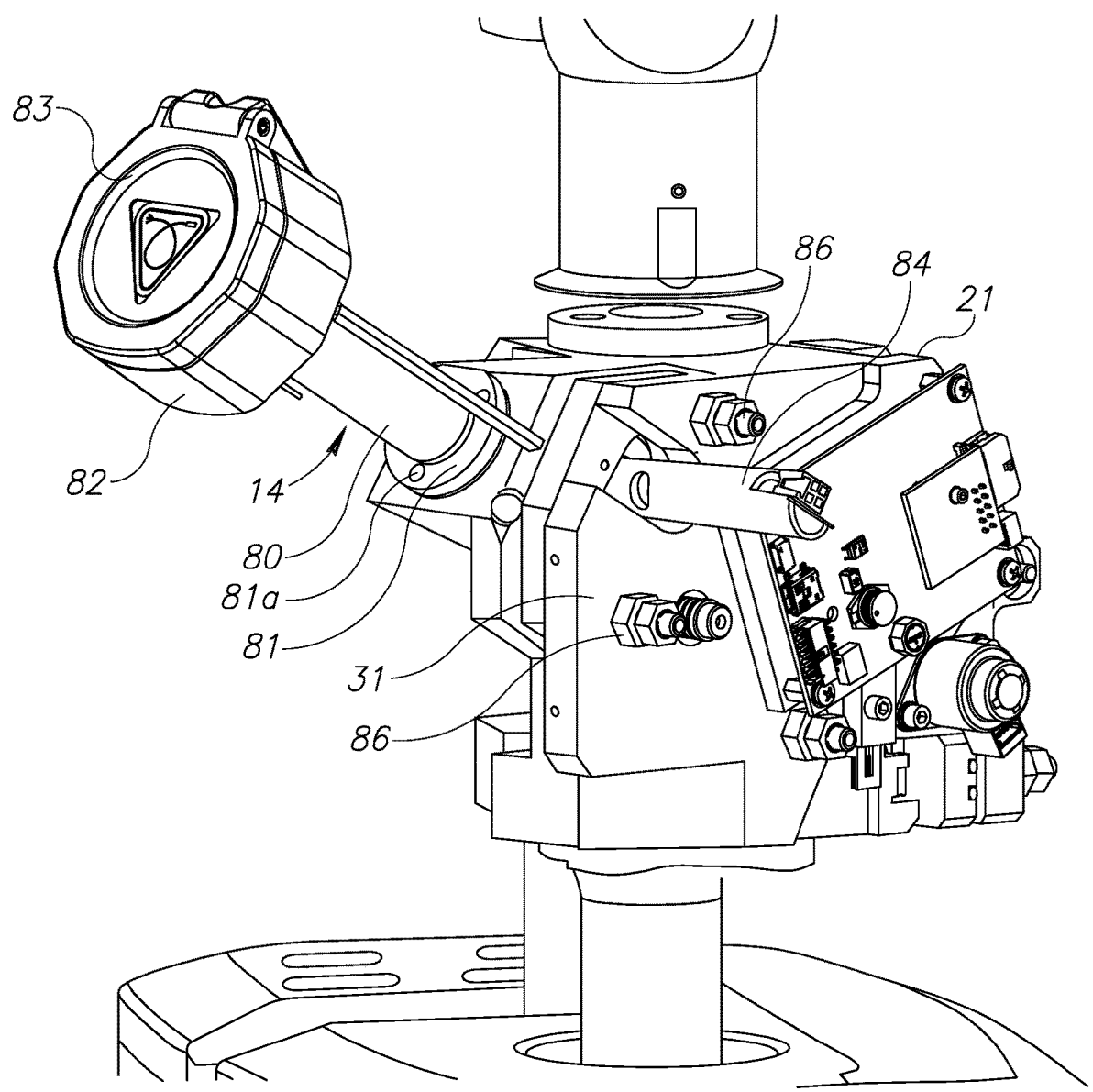
FIG. 11 is a perspective view of part of the adaptor of FIG. 2.
Figure 12:
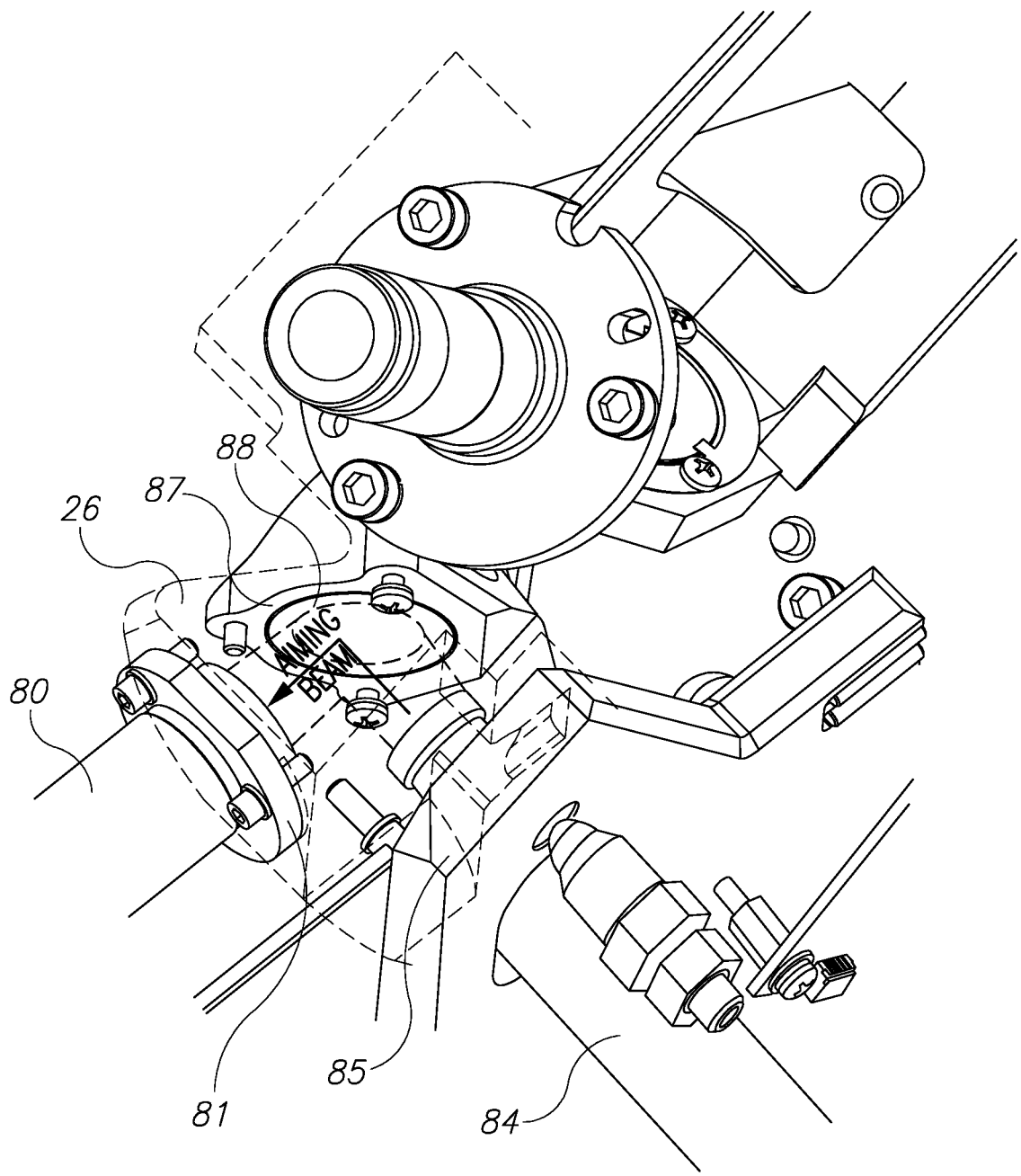
FIG. 12 is a partly transparent perspective view of part of the adaptor of FIG. 2.

The first output port 14 for connection to a flexible wave guide and the auxiliary aiming beam will now be discussed with reference to FIGS. 11 to 14. FIG. 11 is a perspective view of the opto-mechanical chassis 21 showing the output port 14 and the auxiliary guide beam support 31. As seen in FIG. 11, the first output port 14 comprises a cylindrical element 80 with a flange 81 at one end which is connected to the angled surface 27 of the opto-mechanical chassis 21 by bolts 81a received in threaded bores 28. A wave guide connection port 82 is mounted at the opposite end, protected by a lid 83. The auxiliary guide beam source is shown at 84 comprising a red laser diode with its associated electronics mounted in a single element. The auxiliary guide beam 84 is mounted on a support plate 85 which is adjustably connected to the support 31 by adjustable bolts 86. As shown in FIG. 12, the auxiliary guide beam source 84 is directed at a beam combiner comprising an angled mirror 88 supported at the inclined rear surface 32 such that it is set at approximately 45° to the cylindrical part 80 and the auxiliary guide beam source 84. The angled mirror 88 is positioned such that the aiming beam is directed into the first output port 14 and the main laser beam, when directed through first output beam path 24, passes through the mirror 88 substantially undeflected and into third output beam path 26. It will be apparent that the beam acts to combine the main laser beam and auxiliary guide beam when the first output port 14 is in use.

Figure 13A:
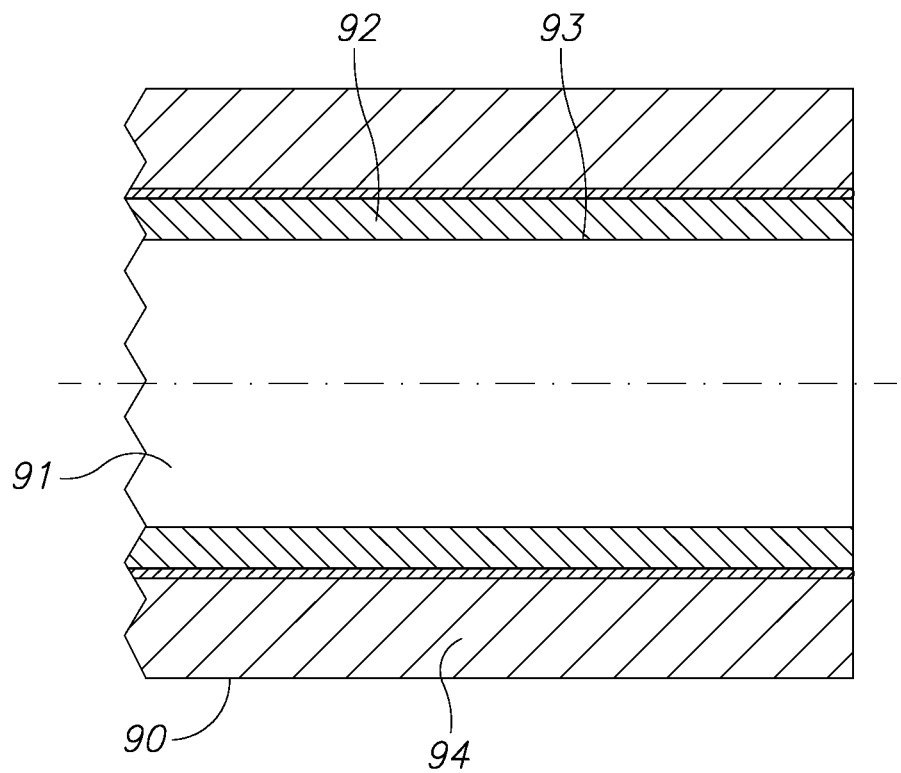
FIG. 13a is a section through a flexible wave guide.
Figure 13B:
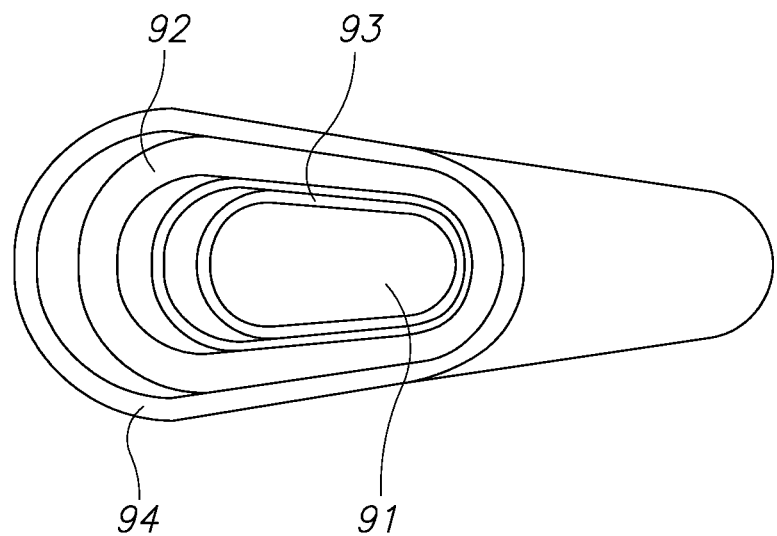
FIG. 13b is a partially cut away perspective view of the wave guide of FIG. 13a, FIG. 14a is a section through the first output port of the apparatus of FIG. 2.

An end part of a flexible wave guide as used herein is shown in 90 in FIG. 13a and FIG. 13b. The flexible wave guide 90 has a hollow core 91 within a silica substrate 92. The inner surfaces of the silicate substrate 92 are coated with a reflective surface 93, in the present example an interface film of silver deposited on the inner surface of the silicate substrate, and then a silver iodide coat deposited on the silver interface film. The silica substrate 92 is surrounded by a protective polymer coating 94.

Figure 14A:
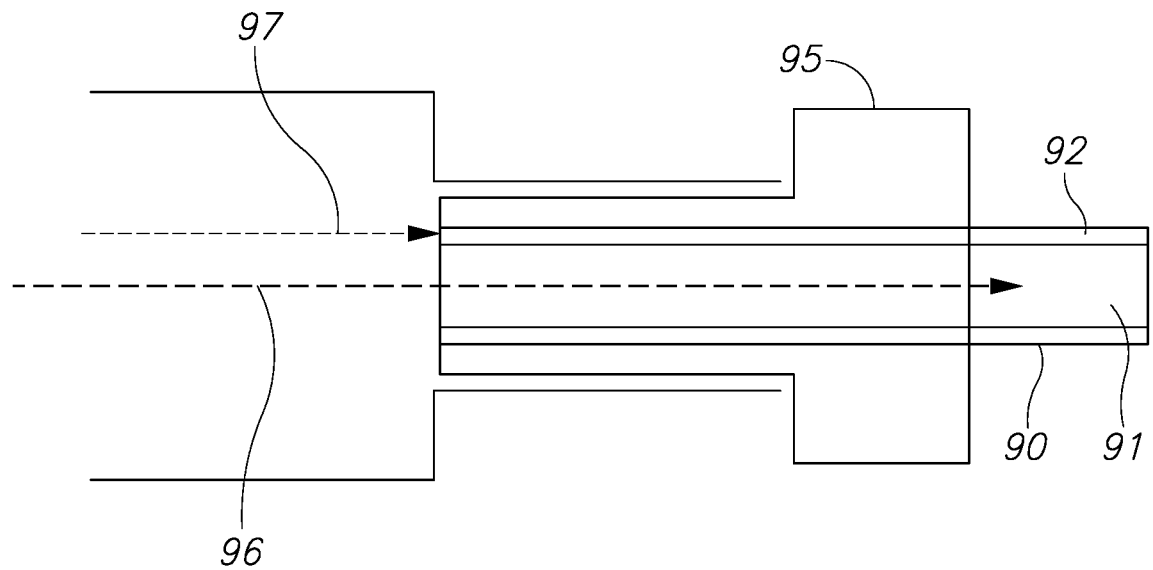
FIG. 14b is a section through an alignment apparatus for the first output port of FIG. 14a, and FIG. 15 is a diametrical illustration of a cooling fluid system to use with the apparatus of FIG. 1.
Figure 14B:
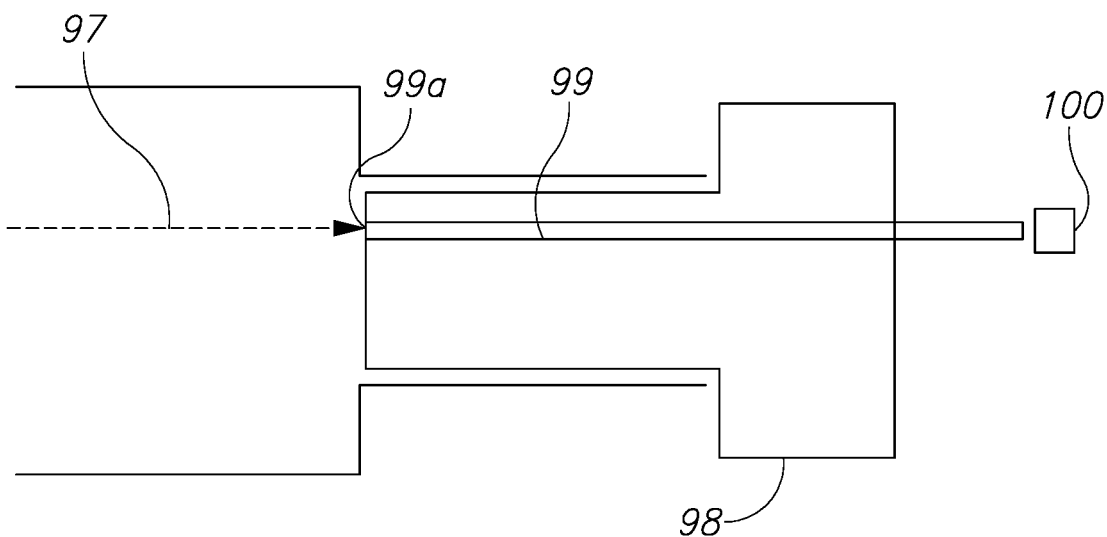
Figure 15:
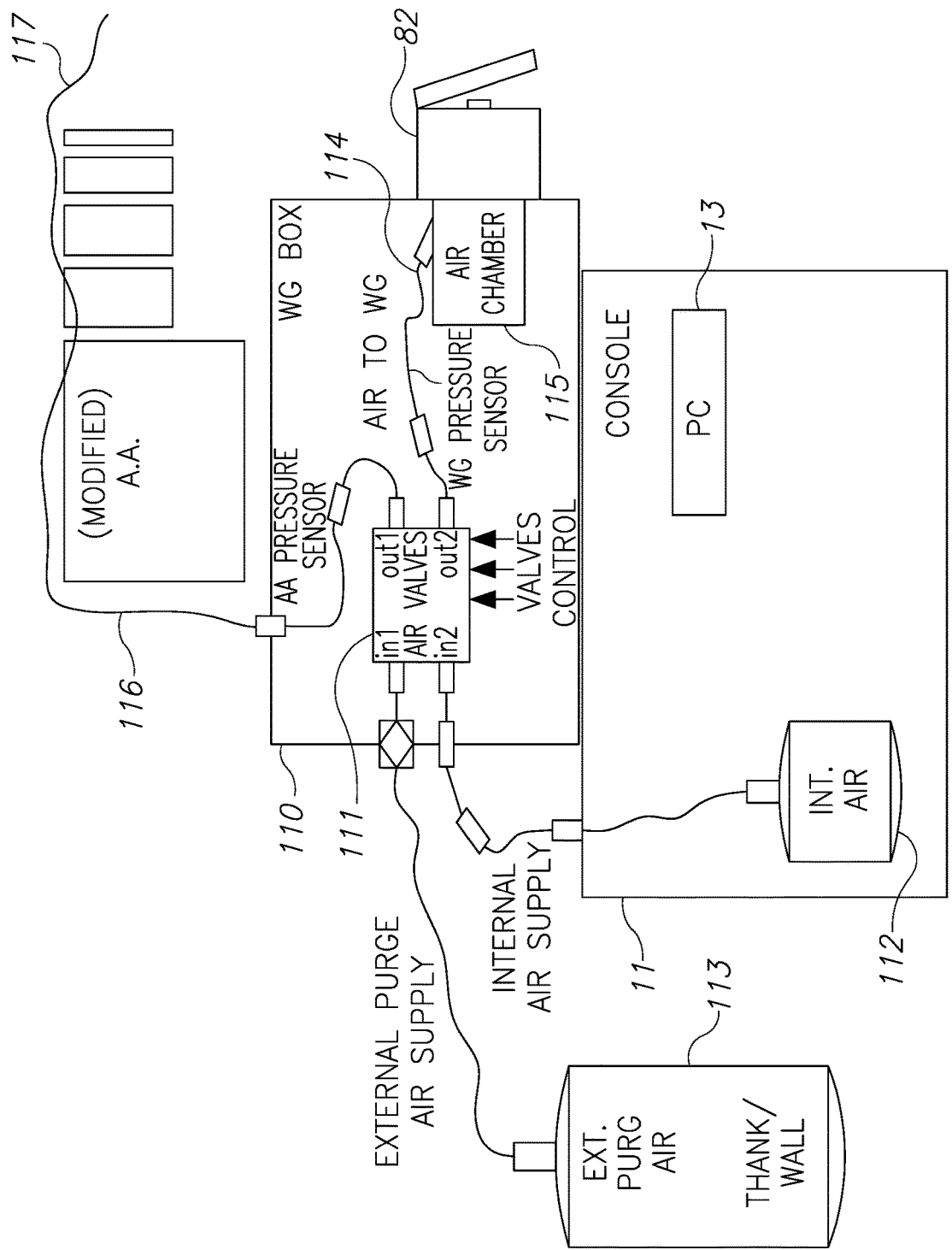

As the auxiliary guide beam will not be reliably propagated down the hollow core 91, in the present example a guide beam is provided by directing the auxiliary guide beam into the silica substrate 92. The bolts 86 are adjusted such that the aiming beam is offset from the main beam as illustrated in FIG. 14a. Referring to FIG. 14a the end of the flexible wave guide is held in a connector 95, and the beams are aligned in such that the main beam 96 is directed into the hollow core 91 and the auxiliary guide beam 97 is offset from the main beam 96 and enters the silica substrate 92. The alignment can be carried using an apparatus such as that shown in FIG. 14b, where a dummy fibre holder 98 is used having the same dimensions as the waveguide holder 95. A conventional optical fibre 99 is held within the dummy fibre holder 98 such that the end 99a of the fibre 99 is at the same offset position as the silica cladding 92 of the flexible wave guide 90. A photodetector 100 is used to measure the light coupled into the alignment fibre 99. Accordingly, the bolts 86 can be adjusted to vary the direction of the auxiliary guide beam 97 to maximise the signal at the photodetector unit 100 to confirm that the auxiliary guide beam is correctly aligned.

To provide cooling, a cooling fluid system is provided, in the present example a pneumatic cooling air system. A suitable cooling system is shown diagrammatically in FIG. 12. The base unit is diagrammatically illustrated at 11 and a pneumatic control apparatus is shown at 110. A distributor is shown at 111 which can receive pressurized from an internal compressor 112 provided within the base unit 11, or from an external source 113, which may be an external tank or an external pneumatic supply system. The distributor 111 is under the control of the control unit in the base unit 11. A first pneumatic connection 114 leads from the distributor 111 to an air chamber 115 located in flow communication with the wave guide connection part 82. A second pneumatic connection 116 is connectible to external flexible air tubes shown diagrammatically at 117 which extend along an outside surface of the articulated arm 16 and direct air towards an accessory or control element at the distal end of the articulated arm 16, for example to be connected to an air inlet of the accessory. The supply of cooling fluid amongst other advantages helps to cool the flexible wave guide, when working at high energies, and also blows smoke or debris away from the operating point of the laser. Where a higher air flow is required, particularly for using a flexible wave guide at high energies, the internal compressor 112 may not be sufficient and the connection to an external source 113 is desirable. Although in the present example suitably filtered and dry compressed air is used, it will be apparent that any other suitable gas or gas mixture may be used.

The present invention is particularly advantageous in that it permits an existing medical laser unit 10 to be retrofitted with an adaptor 15 to provide more flexible operation. Accordingly, a medical laser unit 10 may be adapted by removing pre-existing articulated arm or flexible wave guide connection, and attaching an adaptor 15 to an optical bench part of the base unit 11 as described herein. The method of adapting the medical laser unit may also include connecting the optical wave guide connector part 82 to the control unit, and connecting the auxiliary guide beam laser 80 to the control unit. The actuator is similarly connected to the control unit. In the present example, the adaptor 15 is provided with a dedicated controller 120 mounted on the optical chassis 21, and the auxiliary controller 120 is operable to transmit and receive information to the controller, and control the linear actuator and auxiliary guide beam laser in response to instructions from the controller. Similarly, the pneumatic distributor 111 may be controlled by the auxiliary controller 120 or entirely controlled by the main controller. In operation, the controller may detect the presence of an optical wave guide, or be informed of the presence of the optical wave guide by the auxiliary controller 120 and present options to the operator on the screen. If the operator selects the flexible wave guide, then the auxiliary guide beam laser is actuated, and the actuator is operated to move the switching apparatus to the first position. In the first position, the main laser beam is directed to the first output port 14 and into the flexible wave guide, and the auxiliary guide beam is directed into the silica cladding of the flexible wave guide as discussed herein. The pneumatic distributor 111 is operated to supply air under pressure through the flexible wave guide as discussed above.

Similarly, if the operator selects the articulated arm, the linear actuator is operated to move the mirror assembly to the second position. In this position, the main laser beam and the guide beam are unobstructed and pass through the input beam path, second beam path and are reflected within the articulated arm. Similarly, the pneumatic distributor is operated to supply pressurized air to the articulated arm connection. The auxiliary guide beam laser is not activated as the auxiliary guide beam is not required.

In the alternative, it will be apparent that a medical laser unit may be provided as a new unit with an adaptor 12 already installed. If so, it will be apparent that auxiliary controller 120 may be omitted and the linear actuator, auxiliary guide beam laser and flexible wave guide detector may be directly connectible to and operated by the main control unit. When a medical laser unit is modified to have an adaptor 12, the software in the main control unit may be updated accordingly.

In the above description, an embodiment is an example or implementation of the invention. The various appearances of "one embodiment", "an embodiment" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Furthermore, it is to be understood that the invention can be carried out or practiced in various ways and that the invention can be implemented in embodiments other than the ones outlined in the description above.

Meanings of technical and scientific terms used herein are to be commonly understood as by one of ordinary skill in the art to which the invention belong, unless otherwise defined.

The invention claimed is:

1. A device for directing a CO2 main laser beam along one of two light paths comprising:
   a) a CO2 laser source for producing the CO2 main laser beam;
   b) a first light source for producing a visible to eye main guide beam;
   c) a second light source for producing a visible to eye auxiliary guide beam;
   d) an articulated arm having a distal end and a proximal end, further having a plurality of mirrors being configured to direct and reflect the $CO_2$ main laser beam along a first of the two light paths, the articulated arm also being configured to direct and reflect the visible to eye main guide beam along the first of the two light paths to visualize the $CO_2$ main laser beam on a combined light path from a distal end of the articulated arm towards a target;
   e) a flexible hollow waveguide having a distal end and a proximal end, the waveguide also having a cladding layer surrounding a hollow core extending continuously widthwise between opposite inside surfaces of the cladding layer in a transverse cross section of the flexible hollow waveguide, the cladding layer having an interior cladding layer reflective surface capable of propagating the $CO_2$ main laser beam along the second of the two light paths from the proximal end to the distal end of the waveguide, but unreliably capable of propagating the visible to eye main guide beam from the proximal end to the distal end, thereby precluding visualizing the $CO_2$ main laser beam from the distal end along the second of the two light paths of the flexible hollow waveguide towards the target;

f) an upright base unit, the unit including:
  i) the $CO_2$ main laser beam source being configured to selectively emit a generally vertical $CO_2$ main laser beam to the first or to the second of the two light paths,
  ii) the visible to eye main guide beam source being configured to selectively emit a generally vertical visible to eye main laser beam collimated and co-propagating with the generally vertical $CO_2$ main laser beam to form a generally vertical main beam;
g) a dual port switching adaptor having:
i) a connection portion for mounting of the adaptor to the upright base unit,
ii) an input beam port to receive the generally vertical main laser beam from the base unit,
iii) a first output port for connection of the flexible hollow waveguide at its proximal end, the first output port extending at an angle relative to the input beam port,
iv) a second output port for connection of the articulated arm thereto, the second output port extending substantially vertically in line with the input beam port,
v) an inlet port for connection of a visible to eye auxiliary guide beam source and being capable of selectively emitting the visible to eye auxiliary guide beam,
vi) a switching element moveable between a first position and a second position to direct the $CO_2$ main laser beam to one of the first output port or the second output port, and
vii) a beam combiner for directing the visible to eye auxiliary guide beam to the first output port for passing along the cladding layer, the visible to eye auxiliary guide beam being offset from the $CO_2$ main laser beam; and
f) a control unit configured to control movement of the moveable switching element, activation of the $CO_2$ main laser beam source, activation of the visible to eye main guide beam source, and activation of the visible to eye auxiliary guide beam source: the control unit being configured to cause movement of the moveable switching element to direct the $CO_2$ main laser beam to either the first output port or the second output port wherein:
on directing the $CO_2$ main laser beam to the first output port, the control unit is configured to activate the visible to eye auxiliary light beam source to direct the auxiliary light beam to the beam combiner, the first output port and into the cladding layer of the flexible hollow waveguide for visualizing the $CO_2$ main laser beam on their combined emission from the flexible hollow waveguide towards the target, and on directing the $CO_2$ main laser beam to the second output port, the control unit is configured to activate the visible to eye main guide beam source to direct the main guide beam for visualizing the $CO_2$ main laser beam on their combined emission from the distal end of the articulated arm towards the target.

2. The device of claim 1, wherein the switching element comprises a mirror.

3. The device of claim 2, wherein the mirror is moveable in a linear direction between the first position and the second position.

4. The device of claim 3, further comprising a linear actuator operable to move the switching element between the first position and the second position.

5. The device of claim 1 wherein, in one of the first position and of the second position the switching element extends into the input beam port, and in the other of the first position and second position, is spaced from the input beam port.

6. The device of claim 1 further comprising a cooling fluid connection to supply cooling fluid to the first output port.

7. The device of claim 1, wherein the auxiliary beam source comprises a red diode laser device.

* * * * *